(12) United States Patent
Wang et al.

(10) Patent No.: US 8,530,016 B2
(45) Date of Patent: Sep. 10, 2013

(54) REPELLENT ELASTOMERIC ARTICLE

(75) Inventors: Shiping Wang, Libertyville, IL (US); Ida Berger, Buffalo Grove, IL (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 12/831,520

(22) Filed: Jul. 7, 2010

(65) Prior Publication Data

US 2011/0315047 A1    Dec. 29, 2011

Related U.S. Application Data

(63) Continuation of application No. 11/482,276, filed on Jul. 7, 2006, now abandoned, which is a continuation-in-part of application No. 11/082,138, filed on Mar. 16, 2005, now Pat. No. 7,767,251.

(51) Int. Cl.
| | |
|---|---|
| *B32B 1/08* | (2006.01) |
| *B32B 27/06* | (2006.01) |
| *B32B 27/08* | (2006.01) |
| *B32B 27/30* | (2006.01) |
| *B32B 27/32* | (2006.01) |
| *B32B 27/40* | (2006.01) |
| *A41D 19/00* | (2006.01) |
| *A61B 19/04* | (2006.01) |

(52) U.S. Cl.
USPC ....... 428/36.8; 428/34.1; 428/35.2; 428/35.7; 428/36.6; 428/36.91; 2/161.7; 2/168; 2/167; 427/2.1; 427/2.3

(58) Field of Classification Search
USPC ................ 428/34.1, 35.2, 35.7, 36.4, 36.6, 428/36.8, 36.9, 36.91, 36.92; 427/2.1, 2.3; 2/161.7, 167, 168
See application file for complete search history.

(56) References Cited

U.S. PATENT DOCUMENTS

| | | | |
|---|---|---|---|
| 5,171,611 A | 12/1992 | Porter et al. | |
| 5,691,069 A * | 11/1997 | Lee ............................. | 428/500 |
| 5,736,249 A * | 4/1998 | Smith et al. .................. | 428/447 |
| 5,993,972 A | 11/1999 | Reich et al. | |
| 6,358,557 B1 | 3/2002 | Wang et al. | |
| 6,391,409 B1 | 5/2002 | Yeh et al. | |
| 6,660,339 B1 | 12/2003 | Datta et al. | |
| 6,673,404 B1 | 1/2004 | Yeh et al. | |
| 6,828,387 B2 | 12/2004 | Wang et al. | |
| 2002/0173563 A1 | 11/2002 | Wang et al. | |
| 2004/0047979 A1 | 3/2004 | Qiu et al. | |
| 2004/0126604 A1 | 7/2004 | Wang et al. | |
| 2004/0241201 A1 | 12/2004 | Wang et al. | |
| 2005/0019509 A1 | 1/2005 | Gardner et al. | |

FOREIGN PATENT DOCUMENTS

| | | |
|---|---|---|
| EP | 1 036 810 A2 | 9/2000 |
| EP | 1 036 810 A3 | 9/2000 |
| EP | 1 060 680 A2 | 12/2000 |
| JP | 64 38480 | 2/1989 |
| JP | 2003-213122 A | 7/2003 |
| WO | WO 96/23428 A1 | 8/1996 |
| WO | WO 02/32475 A2 | 4/2002 |

* cited by examiner

*Primary Examiner* — Walter B Aughenbaugh
(74) *Attorney, Agent, or Firm* — Arent Fox LLP

(57) ABSTRACT

The invention described herein includes a repellent elastomeric article with antimicrobial properties particularly useful in industrial and medical fields, such as gloves. The article contains an elastomeric base and a fluid-repellent coating composition that effectively repels both hydrophilic and lipophilic liquids from its surface and inhibits cross-contamination of surfaces. Articles prepared in accordance with the invention reduce the risk of contamination associated with blood and other body fluids, as well as reduce fluid-based visual obstruction and enhance the clarity of medical procedures. The invention also provides a method of reducing the ability of fluids to adhere to the surface of an elastomeric article.

26 Claims, 17 Drawing Sheets above = control
below = treated above = Protegrity® SMT (treated)
below = Esteem® SMT (treated)

above = Protegrity® SMT (treated)
below = Esteem® SMT (treated)

Esteem® SMT (treated)

Protegrity® SMT (treated)

above = untreated Protegrity®
below = treated Protegrity® above = untreated Esteem®
below = treated Esteem®

Figure 20
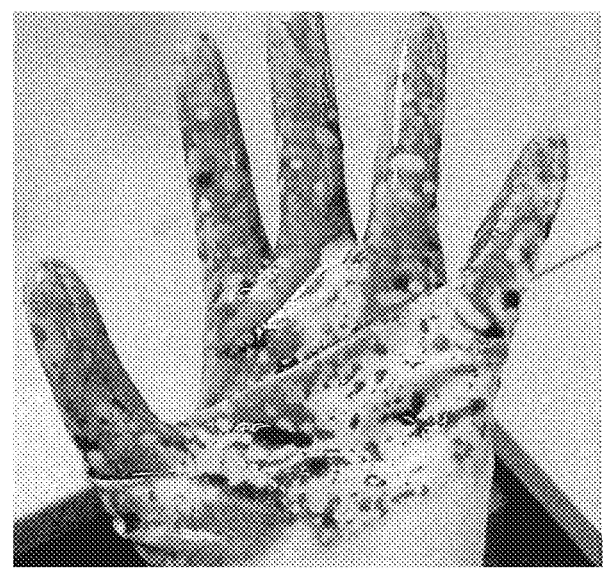
Figure 21

REPELLENT ELASTOMERIC ARTICLE

CROSS-REFERENCE TO RELATED APPLICATION

This application is a continuation of U.S. application Ser. No. 11/482,276, filed Jul. 7, 2006, now abandoned, which is a continuation-in-part of U.S. application Ser. No. 11/082,138, filed Mar. 16, 2005, now U.S. Pat. No. 7,767,251. The disclosures of the prior applications are hereby incorporated by reference in their entirety.

FIELD OF THE INVENTION

The invention relates to elastomeric articles used in medical procedures. In particular, the invention pertains to treated elastomeric articles, such as medical and industrial gloves, which exhibit fluid repellency on the external surface of the article.

BACKGROUND OF THE INVENTION

Elastomeric articles such as gloves often come into contact with liquids and fluids during their use. By their very design and material, articles such as gloves are constructed to form a barrier between the wearer's skin and the exterior environment in which they are to be used.

Medical gloves, including both examination gloves and surgical gloves, are used in healthcare sites and clinical environments and are important in preventing infection and the spread of pathogenic diseases. During use, medical gloves often accumulate blood and other fluids on their surface from the patient's body, thereby contaminating the surface of the glove. Consequently, the wearer of the glove is at increased risk of contamination through contact with the patient's bodily fluids during both use and removal of the glove. Furthermore, during surgical procedures, fluids on glove surfaces can cause visual obstruction and other problems, thereby requiring the user to wipe the gloves or inconveniently remove the gloves and substitute them with another pair during the procedure. Another problem associated with conventional glove usage is that depending on the elastomer used, the gloves can be susceptible to chemical degradation by certain solvents, such as alcohol. Thus, there is a need in the art to provide a surface treatment for gloves and other elastomeric articles which will repel these contaminating fluids from the surface of the articles.

Liquid repellency on an elastomeric article surface such as gloves depends upon the surface tension difference between the contacting liquid and the article surface. Blood and body fluids have both hydrophilic and lipophilic characteristics. Problems have been encountered in formulating effective fluid repellent coatings that utilize a minimal amount of ingredients but at the same time adequately adhere to elastomeric surfaces. Thus, there exists a need in the medical field for elastomeric articles, such as gloves, which effectively repel both hydrophilic and lipophilic fluids from the article surface.

SUMMARY OF THE INVENTION

The invention provides an improved elastomeric article for use in medical procedures, such as gloves, that contains a coating composition that effectively repels both hydrophilic and lipophilic liquids from its surface. Articles such as gloves prepared in accordance with the invention reduce the risk of contamination associated with blood and other body fluids, as well as reduce fluid-based visual obstruction and enhance the clarity of medical procedures with which they are used.

It has been discovered that a coating composition can be formulated which effectively repels both hydrophilic and lipophilic fluids, but which utilizes relatively few ingredients and which further effectively adheres to elastomeric materials. It has further been discovered that a coating composition can be formulated in which the fluid repellency properties are retained following accelerated age and sterilization. The invention is particularly useful in the context of industrial gloves, food contact gloves and medical gloves, such as medical examination and surgical gloves.

In one embodiment, the invention provides an elastomeric article, such as an elastomeric glove, comprising an elastomeric base and a fluid repellent surface coating composition, wherein the coating composition comprises a low surface energy ingredient. In a preferred embodiment, the invention provides an elastomeric article, such as a glove, comprising a fluid repellent surface coating composition, wherein the coating composition comprises a low surface energy ingredient and further comprises a hydrophobic ingredient. In a particularly preferred embodiment, the low surface energy ingredient comprises a water-based fluoropolymer or fluorinated polymer, such as a fluoroalkyl acrylic polymer, and the hydrophobic ingredient comprises a water-based wax, which can be an emulsion or dispersion.

The invention further provides a fluid repellent coating composition for elastomeric articles, said composition comprising a low surface energy ingredient. In a preferred embodiment, the low surface energy ingredient is in combination with a hydrophobic ingredient.

The invention also provides a process for preparing a fluid repellent elastomeric article, such as a glove, comprising: applying a coating composition to the surface of an elastomeric glove, said composition comprising a low surface energy ingredient and, in a preferred embodiment, a hydrophobic ingredient; and drying the article. In addition, the process for preparing industrially produced glove according to the invention can be combined with other processes such as the addition of a lubricant for improved donning performance while maintaining both repellent performance and donning performance.

The invention provides a method of reducing the ability of fluids to adhere to the surface of an elastomeric article comprising applying a fluid repellent coating composition to said surface, said composition comprising a low surface energy ingredient and, in a preferred embodiment, a hydrophobic ingredient.

An additional advantage of the invention is that the fluid-repellent-treated elastomeric articles of the invention can be subjected to sterilization treatments without significantly affecting the repellent properties. Furthermore, the desirable gripping properties of donned articles such as gloves are not significantly compromised by the treatment of the invention.

BRIEF DESCRIPTION OF THE DRAWINGS

The invention is further illustrated by the following figures, none of which are intended to be construed as necessarily limiting the invention.

FIG. 20 is a photograph showing a non-sterile Esteem® polyisoprene surgical glove treated according to the invention and then having been subjected to the water repellency test. See Example 43.

FIG. 21 is a photograph showing a non-sterile Esteem® polyisoprene surgical glove treated according to the invention and then having been subjected to the synthetic blood repellency test. See Example 50.

DETAILED DESCRIPTION OF THE INVENTION

Figure 2:
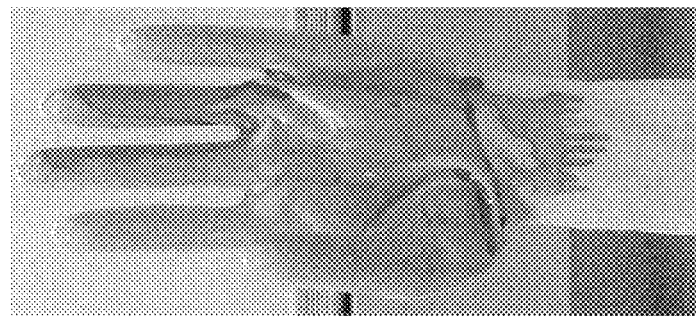
FIG. 2 is a photograph of a non-sterile Esteem® SMT polyisoprene surgical glove untreated (control) as subjected to the water repellency test. See Example 44.

As used herein, the term "repellent" when used in reference to the repellent property associated with the invention, is meant to refer to the functional surface property of resisting chemical or physical interaction such as accumulation, deposition, absorption, penetration, and degradation of liquids when liquids come into contact with the article surface. The term "repellent" is also meant to include the repellency of microorganisms contained in the liquid when it comes into contact with the article surface. Within the context of describing the property of the invention, the term is meant to include the ability to resist adherence of both hydrophilic and lipophilic liquids onto elastomeric materials treated on the surface with a coating composition according to the invention.

A wide variety of elastomeric substrates or bases can be used in conjunction with the invention. Suitable elastomers that can be used as the material for articles prepared according to the invention include natural rubber and synthetic rubbers. Examples of synthetic rubbers that can be used include, but are not limited to, polyisoprene, nitrile rubber, polychloroprene (a.k.a. neoprene), polyvinyl chloride, acrylic copolymers, butyl rubbers, styrene block co-polymers, polyurethane, and combinations thereof. Examples of elastomeric substrates in the form of gloves that are suitable for use with the invention include, but are not limited to: polyisoprene surgical gloves described in Wang et al., U.S. Pat. No. 6,828,387, and under the trade name Esteem® (commercially available from Cardinal Health, Inc., Dublin, Ohio); and natural rubber latex surgical gloves described in Yeh, U.S. Pat. No. 6,673,404, and under the trade name Protegrity® (commercially available from Cardinal Health, Inc., Dublin, Ohio). The entire texts of the referenced patents are incorporated herein by reference. Examples of other elastomeric substrates in the form of gloves that can be used with the invention include Positive Touch® natural rubber gloves (commercially available from Cardinal Health, Inc., Dublin, Ohio) and Syntex® nitrile rubber gloves (commercebally available from Hongray Company, Xinji, China). The invention can also be used with dental gloves, industrial gloves, orthopedic gloves, and the like.

Elastomeric substrates can include gloves as described in Reich et al., U.S. Pat. No. 5,993,927, the entire text of which is incorporated herein by reference. Examples of elastomeric substrates also include Esteem SMT® polyisoprene surgical gloves and Protegrity SMT® natural rubber latex surgical gloves (both commercially available from Cardinal Health, Inc., Dublin, Ohio), in which the base glove has been modified with a treatment formulation containing ammonium salts of alkyl phosphates and other processing additives.

Although the invention is particularly useful in medical gloves, a wide variety of other elastomeric articles can benefit from the advantages associated with the invention and similarly can be used as well. Examples of additional elastomeric articles that can be used include, but are not limited to, finger cots, condoms, catheters, dental dams, wound dressings, and the like. The elastomeric substrate form, or base article itself to be used as part of the invention, can be prepared using well-known and conventional techniques and equipment readily available to those skilled in the art. For example, elastomeric gloves can be prepared using convention mold-dip-cure techniques and equipment. The coating composition of the invention is applied to the surfaces of the formed articles using conventional techniques and equipment readily available to those skilled in the elastomeric article manufacturing field. Such techniques include, but are not limited to, dipping, spraying, brushing, and the like.

When applied to gloves as the elastomeric article, the fluid repellent coating composition can be applied to the exterior surface, interior skin-contacting surface, or both. When present on the interior, skin-contacting surface of a glove, the fluid repellent coating affords the additional advantage of reducing the likelihood of sweat-penetration into the elastomeric material, thereby reducing the deformation effect caused by sweat-penetration of gloves that can occur when the gloves are worn for prolonged periods of time.

Another important advantage of the invention is that when the fluid repellent coating is present on the surface of a glove, desirable grip-ability and donning properties are not substantially compromised by the fluid repellent coating composition. This is because fluid repellency is not the same phenomenon as lubricity. Similarly, the presence of the fluid repellent coating on the exterior surface of the glove does not significantly compromise grip-ability of the glove. As a result, the user of the glove retains the desired level of tactile sensitivity and grasp while wearing and using the glove. Thus, by qualitative inspection, gloves prepared according to the invention maintain grip properties despite the simultaneous property of fluid repellency.

Important advantages of the invention are realized, of course, when the coating composition has been applied to the exterior surface of the elastomeric article. These advantages include the repulsion and quick beading of liquids and fluids coming into contact with the article, e.g., glove. Such liquids include blood, synthetic blood, and other bodily fluids. Fluid repellency is evaluated by measuring the contact angle by placing 0.1 mL of water on the surface of an elastomeric article, photographing the sample, and manually measuring the angle on a printout of the photograph with a protractor. Articles according to the invention exhibit a contact angle preferably greater than about 60 degrees, more preferably greater than about 70 degrees, and particularly preferably greater than about 80 degrees at the time of initial contact.

In addition to reducing the likelihood of undesired fluid contact by the user, an increased and readily observable visual cleanliness or clarity of the exterior surface of the article occurs. Furthermore, the frequency with which articles such as a glove need to be changed during a particular or prolonged procedure is lessened as a result of the article's resistance to fluid adherence.

The fluid repellent surface coating composition comprises a low surface energy ingredient. Low surface energy ingredients that can be used in the invention preferably include water-based fluoropolymers or fluorinated polymers. Examples of fluoropolymers or fluorinated polymers that can be used as the low surface energy ingredient include, but are not limited to, perfluoroalkyl acrylic co-polymer (such as Zonyl® 8300 available from Ciba Specialty, High Point, N.C.; and Scotchban™ FC-845 available from 3M, St. Paul, Minn.), perfluoroalkyl urethane (such as L-8977 available from 3M, St. Paul, Minn.), perfluoropolyether-modified polyurethane dispersion (such as Fluorolink™ P56 available from Ausimont, Thorofare, N.J.), fluorinated silicone polyester (such as Lambent™ WAX available from Lambent Technologies, Fernandina Beach, Fla.), polychlorotrifluoroethylene (such as Aclon™ PCTFE available from Honeywell, Morristown, N.J.), polyvinylidene fluoride dispersion (such as Unidyne™ TG available from Daikin America, New York, N.Y.), tetrafluoroethylene-hexafluoropropylene co-polymer (such as Dyneon™ FEP available from 3M, Parsippany, N.J.), polyperfluoroethoxymethoxydifluoroethyl PEG phosphate (such as Fomblin™ HC/2-1000 available from Solvay Solexis, Houston, Tex.), and combinations thereof. Perfluoro and mixed hydro-fluoro components are envisioned. A preferred low surface energy ingredient is the perfluoroalkyl acrylic co-polymer Zonyl® 8300.

In a preferred embodiment, the fluid repellent surface coating composition further comprises a hydrophobic ingredient. The hydrophobic ingredient in the coating composition can include a water-based wax, by which is meant a heterogeneous wax-based liquid having a continuous phase consisting of water, and a non-aqueous hydrophobic phase. The water-based system, therefore, can be either an emulsion or dispersion as a whole depending upon the process of forming the composition. It will be understood that the terms "emulsion" and "dispersion" (e.g. water-based wax dispersion and water-based wax emulsion) within the context of the invention are referred to herein interchangeably.

Hydrophobic ingredients that can be used include, but are not limited to, water-based systems including water-based wax dispersions or wax derivative dispersions. Examples of water-based wax dispersions that can be used include synthetic wax, halogenated wax, silicone wax, fatty wax, paraffin wax, polyolefin wax, natural wax, and combinations thereof. A preferred hydrophobic ingredient is a water-based wax dispersion known as a fluorochemical extender. Examples of water-based wax dispersions that can be used include, but are not limited to, synthetic wax (such as Freepel® 11225 available from Noveon, Inc., Cleveland, Ohio); polyethylene wax (such as Michem™ ME available from Michelman, Cincinnati, Ohio; Luwax™ AF available from BASF, Parsippany, N.J.; Aquatec™ available from Eastman Chemical, Kingsport, Tenn.; and Jonwax™ available from S.C. Johnson Wax, Racine, Wis.); oxidized polyethylene wax (such as Poligen™ WEI available from BASF, Parsippany, N.J.); ethylene acrylic acid copolymer EAA wax (such as Poligen™ WE available from BASF Parsippany, N.J.); ethylene vinylacetate copolymer wax (such as Aquacer™ available from BYK, Wallingford, Conn.); modified polypropylene wax (such as Aquaslip™ available from Lubrizol, Wickliffe, Ohio); silicone wax (such as DC 2503, DC2-1727, DC C-2-0563, DC 75SF and DC 580 available from Dow Corning, Midland, Mich.; Masilwax™ available from Noveon, Cleveland, Ohio; Silcare™ 41M available from Clariant, Charlotte, N.C.); fluoroethylene wax (such as Hydrocer™ available from Shamrock, Newark, N.J.); Carnauba wax (such as Slip-Ayd™ SL available from Daniel Products, Jersey City, N.J.); Fischer-Tropsch wax (such as Vestowax™ available from Degussa, Ridgefield, N.J.); and ester wax (such as Luwax™ E available from BASF, Parsippany, N.J.; and Lipowax™ available from Lipo, Paterson, N.J.), and combinations thereof. A preferred hydrophobic ingredient is the synthetic wax dispersion Freepel® 1225.

A preferred embodiment for the fluid repellent coating composition is the combination of a perfluoroalkyl acrylic copolymer with a water-based wax dispersion. In one embodiment, a fluoroalkyl acrylic polymer can be present in an amount ranging from about 10% by solid weight to about 0.05% by solid weight of the total coating composition. The wax dispersion can be present in an amount ranging from about 30% by solid weight to about 0.5% solid weight.

In a particularly preferred embodiment, a fluoroalkyl acrylic polymer is present in an amount of about 0.2% to about 2.0% by solid weight of the total coating composition, in combination with the water-based, wax dispersion present in an amount of about 1% to about 10% by solid weight of the total coating composition. Put another way, preferably the ratio of wax dispersion ingredient to fluoroalkyl acrylic polymer ingredient in the coating composition according to total solid weight (content) is about 5 to about 1.

The concentration of the fluoropolymer in the coating composition of the invention can affect the repellency performance. For example, increasing the fluoropolymer concentration also increases repellency as measured by contact angle. The total solids content (TSC) % of the coating composition of the invention can also affect repellency performance. For example, decreasing TSC of the coating composition can increase repellency as measured by contact angle as well.

In general, elastomeric articles such as gloves according to the invention can be prepared using conventional techniques and equipment readily available to those skilled in the elastomeric art. For instance, formers can be dipped into a coagulant composition and subsequently dipped into latex composition, removed and cured in a heated oven. Variations in glove manufacture, for example, are employed in the art. Examples of gloves suitable for use with the invention include, but are not limited to: polyisoprene surgical gloves described in Wang et al., U.S. Pat. No. 6,828,387, or under the trade name Esteem® and Esteem® SMT commercially available from Cardinal Health, Inc. (Dublin, Ohio); and natural rubber latex surgical gloves described in Yeh, U.S. Pat. No. 6,673,404, or under the trade name Protegrity® and Protegrity® SMT commercially available from Cardinal Health, Inc. (Dublin Ohio). The entire texts of the above-referenced patents are incorporated herein by reference. Elastomeric gloves can also be made using conventional former-dipping-curing techniques and apparatuses, such as those described in Yeh, U.S. Pat. No. 6,391,409, the entire text of which is incorporated herein by reference.

The coating composition of the invention can be applied to elastomeric article surfaces using conventional equipment and techniques readily available to those in the field of manufacturing elastomeric articles, including on-line and off-line techniques such as dipping, spraying, tumbling, and the like. Examples of coating techniques are described in Wang, U.S. Patent Publication 20040126604, and Wang, U.S. Patent Publication 20040241201. For preparing surgical gloves, a preferred method of application is off-line spraying. For the preparation of examination gloves, a preferred on-line method of application is dip coating, and a preferred off-line method is the tumbling method of coating. Processes for the preparation of articles according to the invention can be combined with other processes, such as the prior application of lubricant to a surface for improved donnability, without loss of donning or repellent properties. For example, in the preparation of a surgical glove, the migration of trace amounts of repellent formulation to the donning side of the surgical glove does not interfere with the donning properties of the surgical glove.

Once the coating composition according to the invention has been applied to an elastomeric article, the resulting fluid repellent articles prepared according to the invention can then be packaged in accordance with conventional techniques and equipment. For surgical gloves, an additional aspect of the invention is that the fluid repellent treated gloves can be subjected to sterilization without substantially adversely affecting the repellent properties. An example of a conventional sterilization technique used with gloves, for example, that can also be used with the treated articles or gloves of the invention, includes but is not limited to, sterilization with gamma rays. Articles treated according to the invention can be exposed to accelerated aging without having the performance of the article be significantly or adversely affected.

At time of use, the user dons the gloves, for example, and proceeds with the procedure, e.g., medical procedure. It is during the use of the fluid repellent articles of the invention, of course, that the benefits and advantages become fully realized. For example, when double-glove techniques are used, the repellent properties of an outer glove according to the invention can enhance the visibility of damage or puncture to an inner glove.

EXAMPLES

Gloves prepared in accordance with the invention reduce the fluid-based risk of contamination associated with hospital environment, as well as the risk of contamination associated with food manufacturing and processing. Several classes of microorganisms can cause infections, including bacteria, viruses, fungi, parasites, and prions. The routes of transmission vary by type of organism: direct contact, droplets, airborne routes, or transmitted through exposure to blood, bodily fluids, or mucous membranes. Gloves in general provide an adequate barrier protection and prevent contamination when touching visibly or potentially contaminated substrates. The current invention presents a glove, which has enhanced the mode of reduction of microbial affinity and transmission. The invention presents a novel method of testing the reduced capacity for microbial transmission by an elastomeric article such as a glove. Example 56 describes the reduction of microbial transmission by an elastomeric article when glass or other substrate comes into contact with the elastomeric article.

The term "microorganism", "microbe", "microbial", and the like are used interchangeably herein to refer to organisms with significance of causing diseases in a hospital environment or food spoilage in a food production and processing environment. As used herein, the terms refer but are not limited to gram-positive and gram-negative bacteria, fungi, and viruses. "Microbial inoculum" and "inoculum suspension" refer to any liquid or substrate that contains at least one vegetative cell or spore.

The term "substrate" is meant to include any hard or liquid surface, which can be contaminated by microorganisms. Examples of a substrate include biological objects, as such but not limited to the human body, and physical objects with hard or liquid surfaces such as equipment, instruments, furniture, bodily fluids, and irrigating solutions. When used in reference to the testing method associated with the invention, the substrate is meant to refer to surfaces such as, but not limited to, glass, agar, Ringer's irrigating solution, saline, and synthetic blood. The term "substrate" is also meant to include the contaminated surface when it comes into contact with the elastomeric article surface.

The term "microbial transmission level" is meant to refer to the transmitted CFU/ml after contact between the contaminated substrate and the invention article or the control glove. The term "percent recovery" represents the proportion of the titer of transmitted CFUs and the titer of the potential present cells/spores on the contaminated substrate in CFU/ml multiplied by 100. The term CFU/ml herein invention represents Colony Forming Unit per milliliter.

There are a number of art-recognized methods that a person of ordinary skill in the art could use to assess presence of microbes on various types of substrates. Generally, the measurement of microbial titer is used to establish microbial reduction based on activity of antimicrobial/antibacterial-treated materials. These methods include ASTM Method E2149, AATCC Test Method 14-1998 and AATCC Test Method 100-1999. Other test methods specifically address the fluid repellency of a treated article. Methods such as AATCC Test Method 22-2005, AATCC Test Method 70-2005, and AATCC Test Method 118-2002 address water or oil repellency, but fail to incorporate the use of microbes in the testing of repellency of fluids containing microorganisms.

The following non-limiting examples further illustrate the invention. Examples 1-8 describe repellent coating compositions. Examples 9-21 describe gloves made for qualitative and quantitative testing. Examples 22-33 describe post-treatment processes. Examples 34-56 describe various evaluations of the properties of treated articles. The terms "example" and "sample" are used interchangeably when referring to a glove in the following Examples.

Repellent Coating Compositions

Example 1

A formulation in accordance with the invention was prepared by first adding 13 lb of de-ionized water to a dipping tank. This was followed by the addition of 166.06 g of Zonyl® 8300 (perfluoroalkyl acrylic polymer). The mixture was stirred for a period of 30 minutes. The resulting formulation is set forth in the following table:

Table for Example 1

| Ingredient: | Source/Tradename: | Amount (w/w %) |
|---|---|---|
| perfluoroalkyl acrylic polymer (20% solid) | Zonyl ® 8300 | 2.4 |
| Deionized water | | 97.6 |
| Total: | | 100.0 |

(total solids content (TSC) = 0.4%)

Example 2

A coating composition in accordance with the invention was prepared as follows: 40 grams of Freepel®1225 (available from Noveon, Inc., Cleveland, Ohio) and 1 gram of Zonyl® 8300 (available from Ciba Specialty, High Point, N.C.) were added to a 250 ml Erlenmeyer flask containing 60 g of deionized water. Freepel® 1225 is a water-based wax dispersion also known as a fluorochemical extender. Zonyl® 8300 is a composition containing fluorinated acrylic copolymer, hexylene glycol, polyethylene glycol monotridecyl ether and water, and which is in the form of an aqueous polymer dispersion containing a perfluoroalkyl acrylic copolymer having a particle size of about 10 microns. The mixture was continuously stirred for a period of 30 minutes at ambient temperature. The resulting composition contained the following ingredients and amounts:

Table for Example 2

| Ingredient: | Source/Trade name: | Amount (w/w %): |
|---|---|---|
| Perfluoroalkyl acrylic polymer (20% solid) | Zonyl ® 8300 | 1.0 |
| fluorochemical extender emulsion/wax based dispersion (25% solid) | Freepel ® 1225 | 39.6 |
| Deionized Water | | 59.4 |
| Total: | | 100.0 |

Total Solids Content (TSC) = 10.2%

Example 3

In a manner similar to Example 2, the following sample was prepared. C2-056 Repellent is a mixture of organic and inorganic compounds available from Dow Corning, Midland, Mich.

Table for Example 3

| Ingredient: | Source/Trade name: | Amount (w/w %): |
|---|---|---|
| Organic/inorganic repellent mixture (100% solid) | C2-056 Repellent | 10.0 |
| Deionized Water | | 90.0 |
| Total: | | 100.0 |

Total Solids Content (TSC) = 10%

Example 4

In a manner similar to Example 2, the following sample was prepared. Fluorolink® 5049 is a composition containing an anionic perfluoropolyether (PFPE) based polyurethane dispersion in water, polytetrafluoroethylene (PTFE) dispersion, isopropyl alcohol and methyl ethyl ketone, and is available from Solvay Solexis, Thorofare, N.J.

Table for Example 4

| Ingredient: | Source/Trade name: | Amount (w/w %): |
|---|---|---|
| Fluorinated polyurethane anionic resin (30% solid) | Fluorolink ® 5049 | 10.0 |
| Deionized Water | | 90.0 |
| Total: | | 100.0 |

Total Solids Content (TSC) = 3%

Example 5

In a manner similar to Example 2, the following sample was prepared. Fluorolink® S10 is a composition containing a perfluoropolyether (PFPE)-based triethoxysilane dispersion in water, and is available from Solvay Solexis, Thorofare, N.J.

Table for Example 5

| Ingredient: | Source/Trade name: | Amount (w/w %): |
|---|---|---|
| Perfluoropolyether-based triethoxysilane dispersion (100% solid) | Fluorolink ® S10 | 1.0 |
| Isopropyl alcohol | | 95.0 |
| Deionized water | | 4.0 |
| Total: | | 100.0 |

Total Solids Content (TSC) = 1.0%

Example 6

For purposes of comparison, Example 6 is a control, i.e. no treatment.

Example 7

A coating composition in accordance with the invention was prepared as follows: to a 15 lb dipping tank was added 7 lb of deionized water. While stirring continuously, 1360 grams of Freepel® 1225 was added, followed by 34.015 grams of Zonyl® 8300. The solution was stirred for a period of 30 minutes. Then, 6 lb of additional deionized water was added, and the solution was stirred for an additional 30 minutes (% TSC=5.1%).

Example 8

A coating composition in accordance with the invention was prepared as follows: to a dipping tank was added 7 lb of deionized water. Then, 544.24 g of Freepel® 1225 (fluorochemical extender emulsion/wax based dispersion) was added to the water under continuous stirring, followed by the addition of 166.06 g of Zonyl® 8300 (perfluoroalkyl acrylic polymer). After stirring for a period of 30 minutes, 6 lb of additional deionized water was added, and the mixture was stirred for an additional 30 minutes. The resulting formulation is set forth in the following table:

Table for Example 8

| Ingredient: | Source/Tradename: | Amount (w/w %) |
|---|---|---|
| perfluoroalkyl acrylic polymer (20% solid) | Zonyl ® 8300 | 2.4 |
| Fluorochemical extender emulsion/wax based dispersion (25% solid) | Freepel ®1225 | 8.0 |
| Deionized water | | 89.6 |
| Total: | | 100.0 |

(total solids content (TSC) = 2.4%)

Application of Repellent Coating Composition to Glove Surface

Example 9

The formulation of Example 1 was applied to the surface of elastomeric gloves—a non-sterile polyisoprene surgical glove (Esteem® SMT). Each glove was placed on a former and dipped into a solution of the formula of Example 1 for 10 seconds. The gloves were then removed and permitted to drip dry for a period of 10 seconds. The gloves were then placed in an oven to dry for a period of 10 minutes at a temperature of 90° C.

The loading level for the gloves was determined. First, the combined weight of ten untreated gloves of each type was measured. The gloves were treated as described above, and then the ten gloves were weighed. The dry coating weight for the coating was 2.5 mg/glove.

Example 10

An unlubricated surgical glove composed of the elastomeric polyisoprene (e.g. Esteem® SMT Surgical Glove available from Cardinal Health, Inc., Dublin, Ohio) was sprayed with the fluid repellent coating composition of Example 2 of the invention. Using a spray bottle, the coating composition was applied onto the glove surface, with a total of three applications on each side of the glove. The treated gloves were then dried in an oven at a temperature of about 100° C. for a period of about 10 minutes. The gloves were then removed from the oven and cooled to room temperature for a period of 10 minutes.

Examples 11-14

Repellent coating compositions from Examples 3-6 were applied to polyisoprene gloves (Esteem® SMT polyisoprene gloves) in a manner similar to that described above in Example 8 to likewise prepare corresponding treated glove Examples 11-14.

Example 15

Gloves according to the invention were prepared using a dip-coating process, which provides a uniform coating. Polyisoprene gloves (e.g. Esteem® SMT) on formers were dipped in the solution according to Example 7 for a period of 10 seconds, removed and drip dried for a period of 10 seconds. The gloves were then placed in an oven to dry at a temperature of 100° C. for a period of 10 minutes. The dry coating weight for the dip-coating process to prepare polyisoprene gloves using a drying temperature of 100° C. was calculated to be 74 mg/glove.

Examples 16-17

The formulation of Example 8 was then applied to the surface of two different elastomeric gloves—a non-sterile polyisoprene surgical glove (Esteem® SMT) and a sterile natural rubber latex surgical glove (Protegrity® SMT). Each glove was placed on a former and dipped into a solution of Example 8 for 10 seconds. The gloves were then removed and permitted to drip dry for a period of 10 seconds. The gloves were then placed in an oven to dry for a period of 10 minutes at a temperature of 90° C. This procedure was followed for both types of glove.

Loading level for each of the gloves (polyisoprene glove Esteem® SMT (Example 16) and natural rubber latex glove Protegrity® SMT (Example 17)) was determined. First, the combined weight often untreated gloves of each type was measured. The gloves were prepared as described above, and then the ten gloves were weighed. The dry coating weight (loading level) for each of the samples is set forth in the following table:

| Table for Examples 16 and 17 | | |
|---|---|---|
| Sample | Description | Dry coating weight (mg/glove) |
| Example 16 | Treated Esteem ® SMT polyisoprene glove | 15.0 |
| Example 17 | Treated Protegrity ® SMT natural rubber glove | 15.2 |

Examples 16' and 17'

Gloves were prepared in the same manner as Examples 16 and 17. The formulation of Example 8 was applied to the surface of two different elastomeric gloves—a non-sterile polyisoprene surgical glove (Esteem® SMT) (Example 16') and a sterile natural rubber latex surgical glove (Protegrity® SMT) (Example 17').

Examples 18-19

Additional elastomeric substrates in the form of medical examination gloves were prepared with the coating composition in accordance with the invention. In this experiment, the gloves evaluated were Positive Touch® natural rubber gloves (Example 18) and Syntex® nitrile gloves (Example 19).

Initially, the gloves are washed to remove all contaminants from the surface. The glove are inverted and washed on the patient-contacting side twice using a 50 ml of methanol for 2 minutes each wash. The gloves were reverted and dried in an oven at a temperature of 55° C. for a period of 5 minutes, and subsequently cooled to room temperature.

Next, the treated gloves for the experiment were treated with the coating composition described in Example 8 (the Zonyl® 8300/Freepel® 1225 composition) herein above. Gloves of each brand type and elastomeric substrate were placed on a former, dipped in the coating composition for 10 seconds, and drip-dried for 10 seconds. The gloves were then placed in an oven at a temperature of 90° C. for a period of 10 minutes. The descriptions of the samples prepared for comparison are set forth in the following table.

| Table for Examples 18 and 19 | |
|---|---|
| Sample: | Glove Description: |
| Example 18 | Positive Touch ® natural rubber glove (washed/treated) |
| Example 18 untreated control | Positive Touch ® natural rubber glove (washed/untreated) |
| Example 19 | Syntex ® nitrile glove (washed/treated) |
| Example 19 untreated control | Syntex ® nitrile glove (washed/untreated |

Examples 20-21

Additional elastomeric substrates in the form of medical gloves were prepared by the treatment composition in accordance with the invention. In this experiment, the gloves evaluated were Protegrity® natural rubber surgical gloves (Example 20) and Esteem® synthetic polyisoprene surgical gloves (Example 21).

The gloves for the experiment were treated with the coating composition described in Example 8 (the Zonyl 8300/Freepel 1225 composition) herein above. Gloves of each brand type and elastomeric substrate were placed on a former, dipped in the coating composition for 10 seconds, and drip-dried for 10 seconds. The gloves were then placed in an oven at a temperature of 90° C. for a period of 10 minutes. The descriptions of the samples prepared for comparison are set forth as follows:

| Table for Examples 20-21 | |
|---|---|
| Sample: | Glove Description: |
| Example 20 | Protegrity ® natural rubber glove treated |
| Example 20 untreated control | Protegrity ® natural rubber glove untreated |
| Example 21 | Esteem ® polyisoprene glove treated |
| Example 21 untreated control | Esteem ® polyisoprene glove untreated |

Post-Application Treatment of Coated Gloves

Examples 22-27

Accelerated Aging

Protegrity® SMT natural rubber gloves and Esteem® SMT polyisoprene gloves were used for comparatively testing the stability of the coating composition after accelerated age. A control glove, a treated glove, and a treated glove subjected to accelerated age were evaluated. Samples were treated with the coating composition of the invention as found in Example 8 herein above. The stability of the repellent coating after accelerated age was tested by placing the samples in an oven at a temperature of 70° C. for a period of 7 days according to ASTM D 573 for medical gloves for sterile Protegrity® SMT and non-sterile Esteem® SMT gloves.

Samples of each type of glove are summarized in the following table:

Table for Examples 22-27

| Sample: | Glove type: | Description: |
|---|---|---|
| Example 22 | Protegrity ® SMT natural rubber | control |
| Example 23 | Protegrity ® SMT natural rubber | treated |
| Example 24 | Protegrity ® SMT natural rubber | treated and aged (70° C./7 days) |
| Example 25 | Esteem ® SMT polyisoprene | control |
| Example 26 | Esteem ® SMT polyisoprene | treated |
| Example 27 | Esteem ® SMT polyisoprene | treated and aged (70° C./7 days) |

Examples 28-33

Sterilization

The sterilization stability test was carried out using gamma radiation. The sterilized glove samples were exposed to gamma radiation at a range from 28 to 55 kGY (1 kilo Gray=0.1 Mrads) for each of the Protegrity® SMT and Esteem® SMT gloves. A control glove, a treated glove, and a treated glove subjected to gamma sterilization were evaluated. (Note that the Protegrity® SMT glove was sterilized prior to treatment with the Zonyl™/Freepel™ composition of the invention and after treatment. The Esteem® SMT glove was not sterilized prior to the treatment of the invention.) Samples were treated with the Zonyl™/Freepel™ composition of the invention as found in Example 8 herein above. The samples of each type of glove are summarized in the following table:

Table for Examples 28-33

| Sample: | Glove type: | Description: |
|---|---|---|
| Example 28 | Protegrity ® SMT natural rubber | control |
| Example 29 | Protegrity ® SMT natural rubber | treated |
| Example 30 | Protegrity ® SMT natural rubber | treated and sterilized |
| Example 31 | Esteem ® SMT polyisoprene | control |
| Example 32 | Esteem ® SMT polyisoprene | treated |
| Example 33 | Esteem ® SMT polyisoprene | treated and sterilized |

Evaluation of the Properties of Coated Gloves

The mechanical properties of the gloves according to the invention along with the performance of the gloves (i.e., contact angle and qualitative water repellency) clearly depict the durability of the repellent coating. The experiments evaluating these aspects are set forth as follows.
Mechanical Property Evaluation The durability of the coating composition on articles prepared in accordance with the invention was evaluated after being subjected to accelerated age and sterilization tests.

Example 34

Synthetic gloves prepared according to the invention were evaluated for mechanical stability in relation to the accelerated aging stability test. Esteem® SMT synthetic polyisoprene gloves were treated according to Examples 25-27. The tensile strength values and percent elongation values of all three samples were then tested according to ASTM Standard Specification for natural rubber latex gloves ASTM D 3577$^{e2}$. The following table contains the results.

Table for Example 34

| Sample: | Tensile strength: psi ± S.D. | % Elongation ± S.D. |
|---|---|---|
| Example 25 (control, uncoated) | 3000 ± 300 | 770 ± 40 |
| Example 26 (before aging) | 2900 ± 300 | 790 ± 30 |
| Example 27 (after aging) | 2400 ± 700 | 590 ± 60 |

Example 35

Synthetic gloves prepared according to the invention were evaluated for mechanical stability in relation to the sterilization stability test. Esteem® SMT synthetic polyisoprene gloves were treated according to Examples 31-33. The tensile strength values and percent elongation values of all three samples were then tested according to ASTM Standard Specification for natural rubber latex gloves ASTM D 3577$^{e2}$. The following table contains the results.

Table for Example 35

| Sample: | Tensile strength: psi ± S.D. | % Elongation ± S.D. |
|---|---|---|
| Example 31 (control, uncoated) | 3000 ± 300 | 770 ± 40 |
| Example 32 (before sterilization) | 2900 ± 300 | 790 ± 30 |
| Example 33 (after sterilization) | 2800 ± 300 | 720 ± 30 |

As can be seen from the above data, glove tensile strength and elongation of Esteem® SMT synthetic polyisoprene gloves were fairly maintained after aging conditions or sterilization conditions. The mechanical properties of Esteem® SMT gloves are not significantly affected when treated by the coating composition of the invention.
Water Repellancy Testing: Contact Angle Measuring and comparing contact angle over time is a quantifiable method for measuring durability of a repellent coating on a material surface.

Example 36

Contact angle evaluation was performed on a sample coated with the one-component formulation containing Zonyl® 8300 according to Example 9. From this glove sample, a 2.5 cm$^2$ section was removed, and to each sample 0.1 ml of water (a droplet) was deposited onto its surface. A digital photograph was taken immediately following deposition of the droplets and marked as time zero for initial contact angle measurement. A glass vial was placed over each droplet to prevent evaporation for the aged contact angle measurements.

Additional photographs of the droplets were taken at 5 minute and 15 minute intervals. The photographs of the initial time zero and each of the intervals was then printed and manually measured using a protractor. Contact angle data and durability (% ability to maintain angle over time) was calculated, the results for which are set forth in the following table:

Table for Example 36

| Sample | Contact Angle (θ)/Durability (%) | | |
| --- | --- | --- | --- |
| | 0 min | 5 min | 15 min |
| Example 9 | 87° | 80°/92% | 64°/74% |

As can be seen from the above data, the treated polyisoprene glove (treated Esteem® SMT) exhibits a significantly larger initial contact angle measurement and maintains higher contact angle values over a greater time period than its untreated counterpart (see the untreated control for Example 16' in the table for Example 38). This sample clearly displays the coating's durability, maintaining over 70% of its original starting contact angle over a 15 min interval. Therefore, there is a significant improvement in the repellency of the glove after being treated with the one-component formulation containing Zonyl® 8300.

Example 37

Examples 10-14 were used, where Example 14 was an untreated glove which served as the control. Each glove was evaluated for water repellency properties through a contact angle test and the results were compared, as follows.

From each glove sample, a 2.5 cm$^2$ sample was cut. To each sample surface, a 0.1 ml water droplet was added onto the sample surface. A digital photograph was taken of each water droplet immediately and labeled as 0 time for the initial contact angle measurement. A glass vial was placed over each droplet to prevent evaporation for the aged contact angle measurements. A second digital photograph was taken at 7 hours for the aged contact angle measurement. The photographs were printed and the contact angle was measured for each pairing of 0 time and 7 hours time using a protractor. The results are set forth in the following table:

Table for Example 37

| Sample/Formula | Contact Angle (θ) (0 time) | Aged Contact Angle (θ) (7 hours) |
| --- | --- | --- |
| Example 10 | 80° | 50° |
| Example 11 | 74° | 45° |
| Example 12 | 70° | 47° |
| Example 13 | 62° | 20° |
| Example 14 (untreated) | 63° | 30° |

As can be seen from the above data, the glove sample treated with the coating formulation from Example 2 exhibits the highest contact angle when compared to the remaining samples. The higher the contact angle measurement, the greater the water repellency. Therefore, according to the contact angle test, gloves prepared according to the invention would exhibit relatively high water repellency properties.

Example 38

Contact angle evaluation was performed on Example 16' and Example 17' as well as untreated controls for each of the examples. From each glove, a 2.5 cm$^2$ section was removed, and to each sample 0.1 ml of water (a droplet) was deposited onto its surface. A digital photograph was taken immediately following deposition of the droplets and marked as time zero for initial contact angle measurement. A glass vial was placed over each droplet to prevent evaporation for the aged contact angle measurements.

Additional photographs of the droplets were taken at 5 minute, 15 minute and 6 hour time intervals. Three photographs of each sample were taken per interval. The photographs of the initial time zero and each of the intervals was then printed and manually measured using a protractor. Contact angle data and durability (% ability to maintain angle over time) was calculated, the results for which are set forth in the following table:

Table for Example 38

| Sample | Contact Angle (°)/Durability (%) | | | |
| --- | --- | --- | --- | --- |
| | 0 min | 5 min | 15 min | 360 min |
| Example 16' | 105° | 100°/95% | 94°/90% | 67°/64% |
| control (untreated Example 16') | 68° | 67°/99% | 33°/48% | 28°/41% |
| Example 17' | 89° | 73°/95% | 73°/95% | 52°/58% |
| control (untreated Example 17') | 20° | 10°/50% | 0°/0% | 0°/0% |

As can be seen from the above data, Example 16' (treated Esteem® SMT polyisoprene glove) and Example 17' (treated Protegrity® SMT natural rubber glove) exhibit significantly larger initial contact angle measurements and maintain high contact angle values over a greater time period than do their untreated counterparts. Furthermore, Examples 16' and 17' clearly display their durability over the 6 hour time frame by maintaining over 50% of their original starting contact angle. Therefore, superior repellency would be associated with gloves prepared according to the invention when used over relatively short time periods (e.g., 5 and 15 minutes) as well as relatively longer time periods sometimes associated with surgical procedures (e.g., 6 hours).

Example 39

Contact angle was measured for each of Examples 22-27. From each glove, a 2.5 cm$^2$ section was removed, and to each sample 0.1 ml of water (a droplet) was deposited onto its surface. A digital photograph was taken immediately following deposition of the droplets and marked as time zero for initial contact angle measurement. A glass vial was placed over each droplet to prevent evaporation for the aged contact angle measurements. Measurements were taken at zero (0) time (initial contact time) and 15 minutes for each sample. The results are set forth in the following table.

Table for Example 39

| Sample: | Description: | 0 time | 15 minutes |
| --- | --- | --- | --- |
| Example 22 | Protegrity ® SMT control | 20° | 0° |
| Example 23 | Protegrity ® SMT treated | 89° | 73° |
| Example 24 | Protegrity ® SMT treated and aged | 103° | 86° |
| Example 25 | Esteem ® SMT control | 68° | 33° |
| Example 26 | Esteem ® SMT treated | 105° | 94° |
| Example 27 | Esteem ® SMT treated and aged | 129° | 70° |

As can be seen from the above contact angle data, gloves treated and subjected to the accelerated age still displayed good water repellency properties as compared to gloves treated but not subjected to the accelerated age.

Example 40

In a manner similar to Example 39, the Examples 28-33 were evaluated for contact angle values. The following table contains the contact angle data for the sterilization stability test:

Table for Example 40

| Sample: | Description: | 0 time | 15 minutes |
|---|---|---|---|
| Example 28 | Protegrity ® SMT control | 20° | 0° |
| Example 29 | Protegrity ® SMT treated | 89° | 73° |
| Example 30 | Protegrity ® SMT treated and sterilized | 83° | 67° |
| Example 31 | Esteem ® SMT control | 68° | 33° |
| Example 32 | Esteem ® SMT treated | 105° | 94° |
| Example 33 | Esteem ® SMT treated and sterilized | 103° | 75° |

As can be seen from the above data, glove samples treated according to the invention and subjected to gamma sterilization conditions still exhibited desirable water repellency properties as measured by contact angle test.

Example 41

In a manner similar to Example 39, the Examples 18 and 19 as well as untreated controls were evaluated for contact angle values, the measurements also being taken at 0 minute and 15 minute time intervals. The results are set forth in the following table.

Table for Example 41

| Sample: | 0 minutes | 15 minutes |
|---|---|---|
| Example 18 | 120° | 100° |
| control (untreated Example 18) | 85° | 81° |
| Example 19 | 100° | 100° |
| control (untreated Example 19) | 0° | 0° |

As can be seen from the above data, gloves treated with the coating composition according to the invention exhibit improved repellency properties as compared to their respective untreated versions. Further, even more significant repellency properties (a difference of 100°) were observed in the treated Syntex® nitrile gloves (Example 19) as compared to the untreated Syntex® glove version.

Example 42

In a manner similar to Example 39, the Examples 20 and 21 as well as untreated controls were evaluated for contact angle values, the measurements also being taken at 0 minute and 15 minute time intervals. The results are set forth in the following table.

Table for Example 42

| Sample: | 0 minutes | 15 minutes |
|---|---|---|
| Example 20 | 75° | 73° |
| control (untreated Example 20) | 0° | 0° |
| Example 21 | 111° | 80° |
| control (untreated Example 21) | 38° | 33° |

Water Repellancy: Qualitative Evaluation

Water repellency was evaluated qualitatively by visual inspection as shown in the following examples.

Example 43

Figure 4:
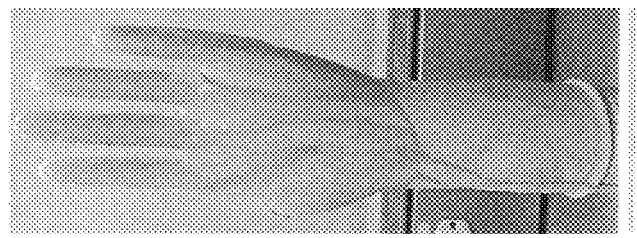
FIG. 4 is a photograph of an untreated non-sterile Esteem® SMT polyisoprene surgical glove (control) as subjected to the water repellency test. See Example 45.

The glove sample of Example 9 was evaluated for water repellency properties as follows. The sample of Example 9 was placed on a hand former and immersed into an aqueous solution containing water and FD&C Red Dye #40. The sample was then withdrawn and photographed. FIG. 20 shows the post-dipped glove of the one-component repellent formulation. FIGS. 2 and 4 show post-dipped gloves of corresponding untreated controls. As can be clearly seen from the photographs, gloves prepared using only Zonyl® 8300 exhibit a distinctive beading of fluid, in contrast to the untreated control gloves which exhibit visible runs and streams of fluid adhering to the glove surface. Therefore, elastomeric gloves treated with the composition of the invention exhibit significantly better fluid repellency as compared to untreated gloves.

Example 44

The water repellency test was conducted on gloves (e.g. Esteem® SMT polyisoprene gloves) treated according to the invention using the formula of Example 2 and untreated gloves (control sample) to evaluate comparative water repellency properties.

Figure 1:
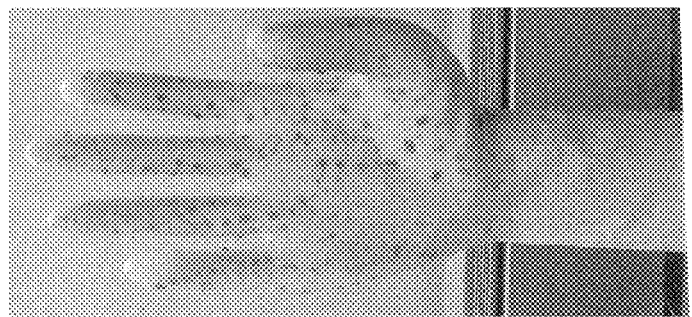
FIG. 1 is a photograph of a non-sterile Esteem® SMT polyisoprene surgical glove treated in accordance with one embodiment of the invention as subjected to the water repellency test. See Example 44.

Each glove was donned and subsequently immersed into a 4 L beaker filled with a 2 L composition of water and FD&C Red #40 dye. The gloves were then visually examined for water repellency on their respective surfaces. Photographs were taken of both gloves to demonstrate the water repellency on their surfaces: FIG. 1 is a photograph of the glove treated with the formula of Example 2 according to the invention after dipping in the water/dye composition. FIG. 2 is a photograph taken of the untreated control glove after dipping in the water/dye composition.

As can be seen from these photographs, the untreated glove of FIG. 2 displayed running dye solution over its entire surface. In contrast, the glove prepared according to the invention and shown in FIG. 1 displayed distinctive tiny beading, which were also observed to quickly run off the glove during testing. Therefore, better water repellency is associated with the gloves prepared according to the invention as compared to untreated gloves.

Example 45

Gloves were prepared according to Example 16 (Esteem® SMT polyisoprene gloves) and Example 17 (Protegrity® SMT natural rubber gloves) as well as untreated gloves (control samples) to evaluate comparative water repellency properties. The samples and descriptions tested were set forth in the following table:

| Table for Example 45 | |
| --- | --- |
| Sample: | Glove Description |
| Example 16 | Treated Esteem ® SMT polyisoprene glove |
| control | Untreated Esteem ® SMT polyisoprene glove |
| Example 17 | Treated Protegrity ® SMT natural rubber glove |
| control | Untreated Protegrity ® SMT natural rubber glove |

Each of the samples were subjected to water repellency test. Each sample was placed on hand formers and immersed into an aqueous solution containing water and FD&C Red Dye #40. Each of the samples was then withdrawn and photographed.

Figure 3:
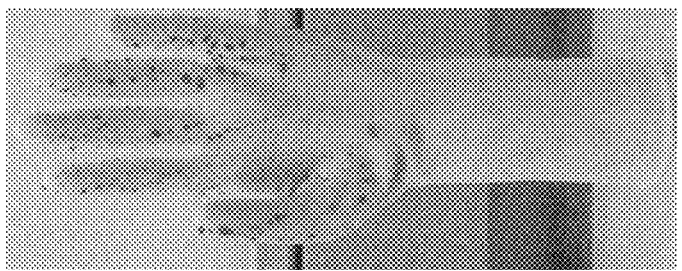
FIG. 3 is a photograph of a non-sterile Esteem® SMT polyisoprene surgical glove treated with a coating according to one embodiment of the invention as subjected to the water repellency test. See Example 45.
Figure 6:
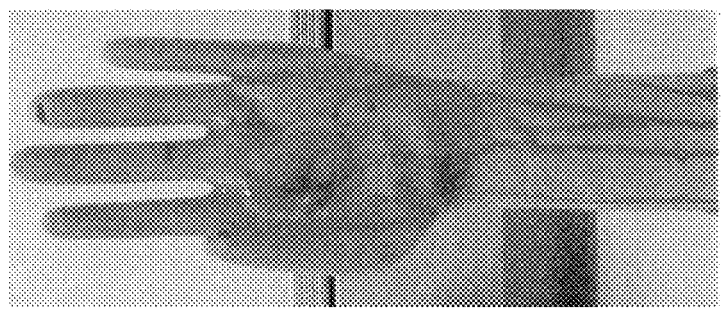
FIG. 6 is a photograph of an untreated sterile Protegrity® SMT natural rubber surgical glove (control) as subjected to the water repellency test. See Example 45.
Figure 5:
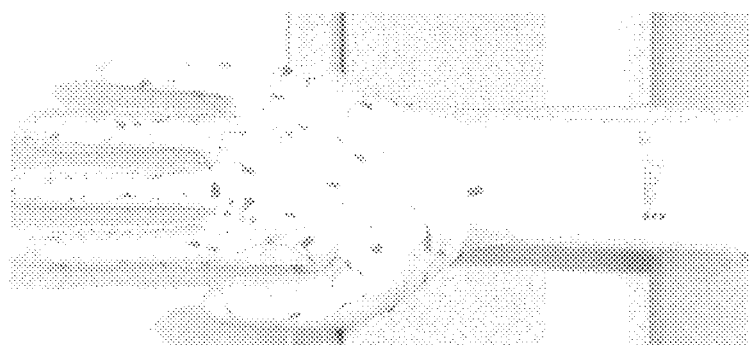
FIG. 5 is a photograph of a sterile Protegrity® SMT natural rubber surgical glove treated with a coating according to one embodiment of the invention as subjected to the water repellency test. See Example 45.

FIG. 3 shows the post-dipped glove of Example 16 of the invention, and FIG. 4 shows the post-dipped glove of the corresponding untreated control. FIG. 5 shows the post-dipped glove of Example 17 of the invention, and FIG. 6 shows the post-dipped glove of the corresponding untreated control. As can be clearly seen from the photographs of the figures, gloves prepared according to the invention containing the combination of Freepel® 1225 and Zonyl® 8300 exhibit distinctive beading of fluid, in contrast to the untreated control gloves which exhibit visible runs and streams of fluid adhering to the glove surface. Therefore, elastomeric gloves treated with the composition of the invention exhibit significantly greater fluid repellency as compared to untreated gloves.

Example 46

Figure 10:
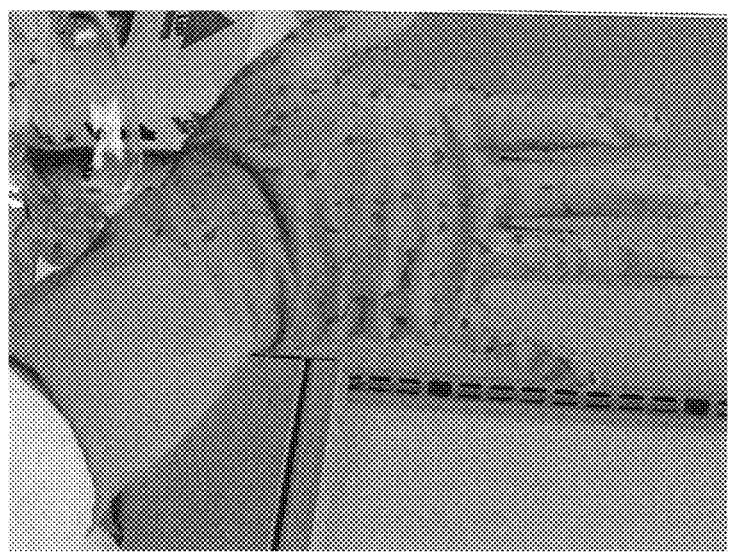
FIG. 10 shows two photographs: a sterile Protegrity® SMT natural rubber surgical glove treated according to one embodiment of the invention and a non-sterile Esteem® SMT polyisoprene surgical glove treated according to one embodiment of the invention, both samples having been subjected to accelerated age followed by the water repellency test. See Example 46.
Figure 10:

Gloves made according to the invention and subjected to accelerated aging were visually inspected for water repellancy, as follows. Example 24 (Protegrity® SMT glove) and Example 27 (Esteem® SMT glove) are shown in FIG. 10. As can be seen from the photographs, both the Protegrity® SMT and Esteems-4 SMT gloves subjected to accelerated aging exhibited substantially visible and readily apparent water repellency. Furthermore, the Esteem® SMT glove sample contained very few droplets on its surface.

Example 47

Figure 12:
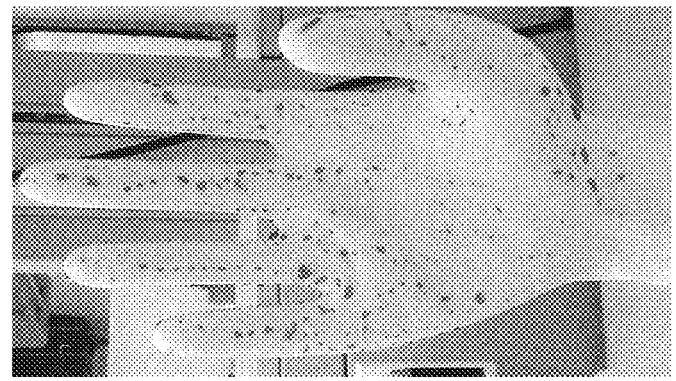
FIG. 12 is two photographs showing a sterile Protegrity® SMT natural rubber surgical glove treated according to one embodiment of the invention and an initially non-sterile Esteem® SMT polyisoprene surgical glove treated according to one embodiment of the invention, both samples having been subjected to further sterilization followed by the water repellency test. See Example 47.
Figure 12:
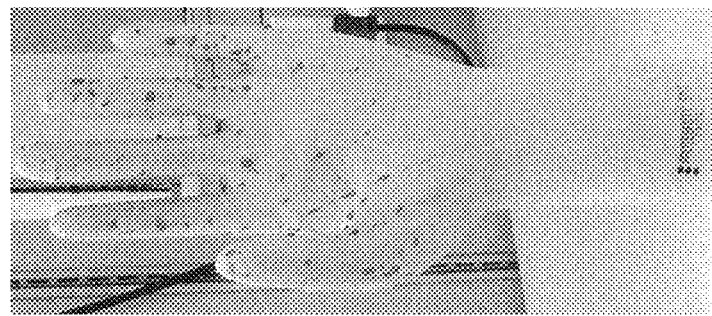

Gloves made according to the invention and subjected to sterilization were visually inspected for water repellancy, as follows. Example 30 (Protegrity® SMT) and Example 33 (Esteem® SMT) were treated according to the invention and subjected to sterilization and then further subjected to the water repellency test, as shown in FIG. 12. As can be seen from the photographs, Protegrity® SMT gloves and Esteem® SMT gloves prepared according to the invention exhibit significant and substantial water repellency properties.

Example 48

Example 18 (Positive Touch® natural rubber gloves) and Example 19 (Syntex® nitrile gloves) and corresponding controls were placed on hand formers and immersed in a 2 liter volume aqueous solution of FD&C red #40 and water. Upon removal from the solution, the beading properties of each glove sample were observed and photographed.

Figure 14:
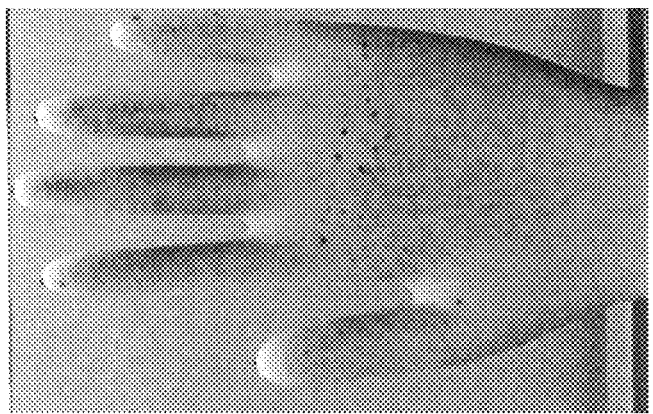
FIG. 14 is two photographs showing a Positive Touch® natural rubber examination glove untreated and another Positive Touch® examination glove treated according to the invention, both samples having been subjected to the water repellency test. See Example 48.
Figure 14:
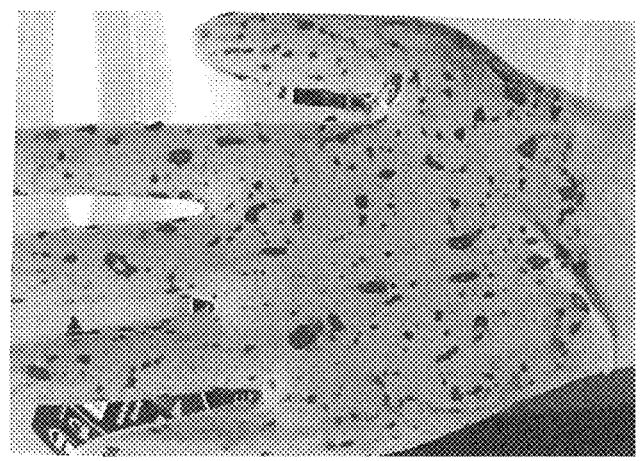
Figure 15:
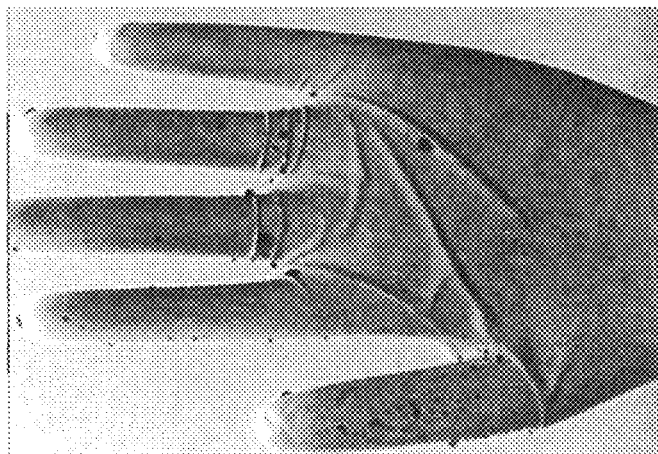
FIG. 15 is two photographs showing a Syntex® synthetic nitrile examination glove untreated and another Syntex® synthetic nitrile examination glove treated according to the invention, both samples having been subjected to the water repellency test. See Example 48.
Figure 15:
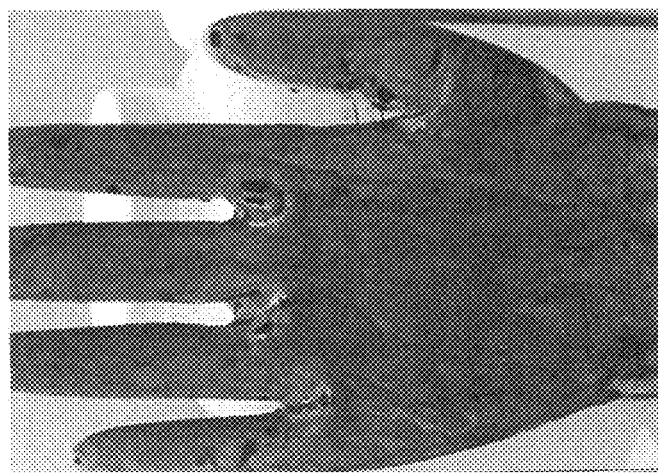

FIG. 14 shows two photographs (Example 18 and its untreated control) side-by-side after being subjected to the water repellency test. FIG. 15 shows two photographs (Example 19 and its untreated control) side-by-side after being subjected to the water repellency test. As can be seen from the photographs, both gloves that were treated according to the invention exhibited very little beading on their surfaces, thereby demonstrating better water repellency in contrast to untreated samples of the corresponding glove type.

Based on the water repellency test set forth above, the invention improves the repellency properties of elastomeric articles composed of natural rubber, as well as those composed of synthetic nitrile elastomers.

Example 49

Example 20 (Protegrity® natural rubber gloves) and Example 21 (Esteem® polyisoprene gloves) and corresponding controls were placed on hand formers and immersed in a 2 liter volume aqueous solution of FD&C red #40 and water. Upon removal from the solution, the beading properties of each glove sample were observed and photographed. The photographs of each sample can be seen in FIGS. 16 and 17.

Figure 16:
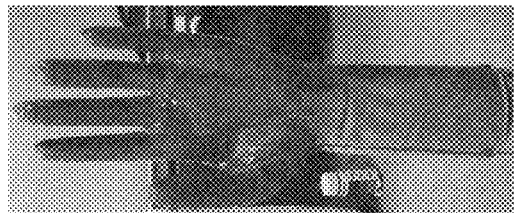
FIG. 16 is two photographs showing a sterile Protegrity® natural rubber surgical glove treated according to the invention alongside another sterile Protegrity® natural rubber surgical glove untreated, both gloves having been subjected to the water repellency test. See Example 49.
Figure 16:
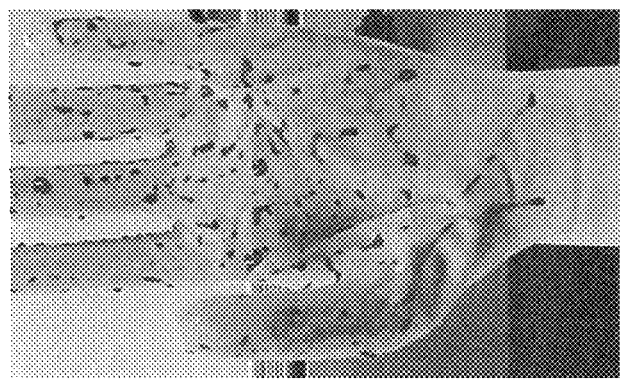

As can be seen in FIG. 16, the sterile Protegrity® natural rubber glove treated and prepared according to the invention exhibited limited surface beading of liquid, whereas the untreated sterile Protegrity® glove shows a continuous smear still present over the entire immersed surface of the glove.

Figure 17:
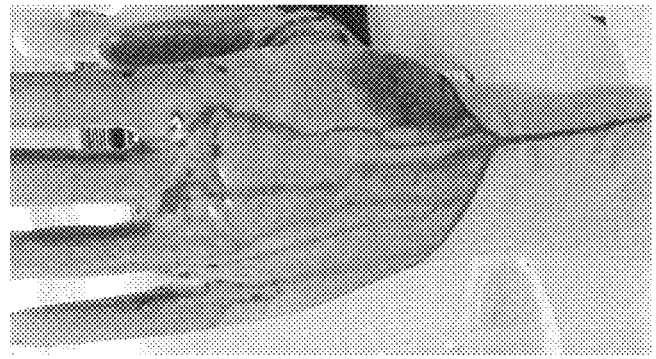
FIG. 17 is two photographs showing a sterile Esteem® polyisoprene surgical glove treated according to the invention alongside another sterile Esteem® polyisoprene surgical glove untreated, both gloves having been subjected to the water repellency test. See Example 49.
Figure 17:

Turning now to FIG. 17, the sterile Esteem® polyisoprene glove sample treated according to the invention exhibits limited beading again. Again, the untreated sterile Esteem® glove contains a continuous coating of the liquid over the entire immersed surface of the glove, along with running of the liquid.

As can be seen from the above data, glove samples prepared in accordance with the invention exhibited significantly improved repellency properties as compared to their untreated counterparts. This was true for both natural rubber gloves and synthetic polyisoprene gloves absent intervening surface treatments, such as their SMT counterpart versions.

Comparative Synthetic Blood Repellency Test

The purpose of this test was to simulate the interaction of gloves (treated and untreated) with human blood as would be encountered in a surgical procedure. Human blood is a complex liquid containing a diverse combination of biochemical materials resulting in properties including: surface tension ranging from about 37 to about 58 dynes/cm; viscosity range from about 3 to about 4 mPa; and pH of about 7.35 to about 7.45. Human blood exhibits characteristics of both pure water as well as hydrophobic liquids, such as hydrocarbons. Synthetic Blood Reagent (available from Johnson, Moen & Co., Rochester, Minn.) was selected to be studied as a substitute of human blood in this invention because its physico-chemical properties (surface tension ranging of about 40 dynes/cm; viscosity of about 3.020 to about 7.70 mPa; and pH 8 to 9) are similar to human blood. Thus the synthetic blood repellency test demonstrates repellency properties that would be similar to that of natural human blood.

Example 50

Figure 8:
FIG. 8 is a photograph of a non-sterile Esteem® SMT polyisoprene surgical glove (untreated control) sample as subjected to the synthetic blood repellency test. See Example 51.

The glove treated with the single component formulation containing Zonyl 8300 according to Example 9 was donned, immersed into an aluminum tray containing synthetic blood, and withdrawn for observation of repellency. The results were photographed and appear as shown in FIG. 21. As can be seen from the photograph, the treated glove displays synthetic blood repellency. An untreated control (Esteem® SMT polyisoprene glove) exhibited almost complete adherence of the synthetic blood on its respective surfaces, as shown in FIG. 8. In contrast, the treated Esteem® SMT glove with the one-component formulation containing Zonyl® 8300 exhibited a difference upon withdrawal, as shown in FIG. 21.

Example 51

Figure 7:
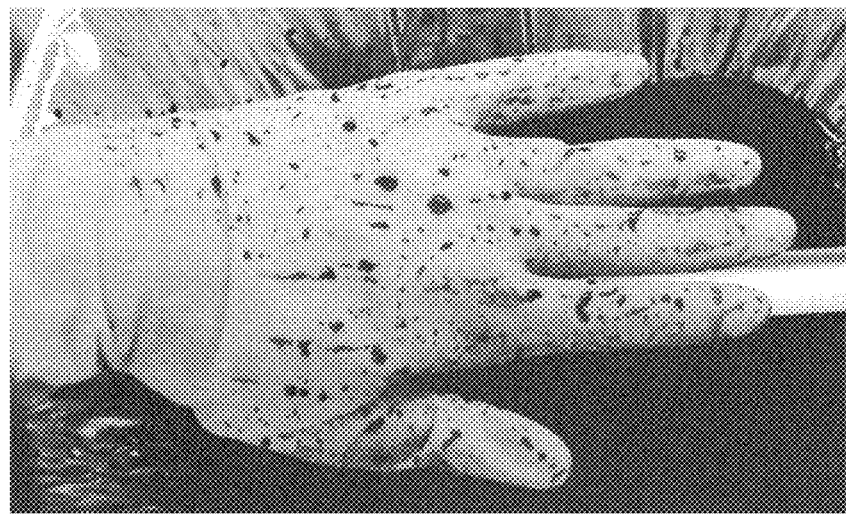
FIG. 7 is a photograph of a non-sterile Esteem® SMT polyisoprene surgical glove treated with a coating according to one embodiment of the invention as subjected to the synthetic blood repellency test. See Example 51.
Figure 9:
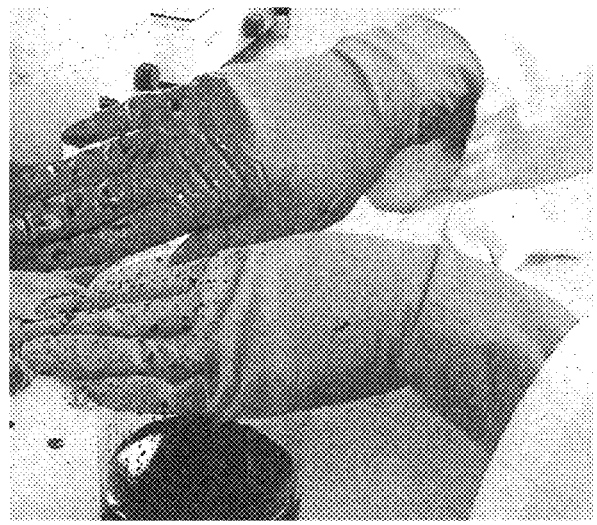
FIG. 9 is a photograph showing two side-by-side sterile Protegrity® SMT natural rubber surgical gloves with one glove treated according to one embodiment of the invention, and the other untreated control, both gloves having been subjected to the synthetic blood repellency test. See Example 51.

Gloves were prepared according to Example 16' (Esteem® SMT polyisoprene gloves) and a control, and according to Example 17' (Protegrity® SMT natural rubber gloves) and a control. Each of the gloves were donned, immersed into a 4 liter aluminum tray containing synthetic blood, and withdrawn for observation of repellency. The results were photographed and appear as shown in FIG. 7 (Example 16'), FIG. 8 (Example 16' control), and FIG. 9 (Example 17' and control).

As can be seen from the photographs, the untreated gloves of Esteem® SMT (natural rubber) and Protegrity® SMT (polyisoprene) exhibited almost complete adherence of the synthetic blood on their respective surfaces. In contrast, the Esteem® and Protegrity® gloves prepared in accordance with the invention exhibited a substantial difference in appearance and relatively small sized beading over the surface which formed rapidly upon withdrawal of the gloves from the. The examples according to the invention demonstrate comparatively superior "blood" repellency property as can be clearly seen from the photographs.

Example 52

Figure 11:
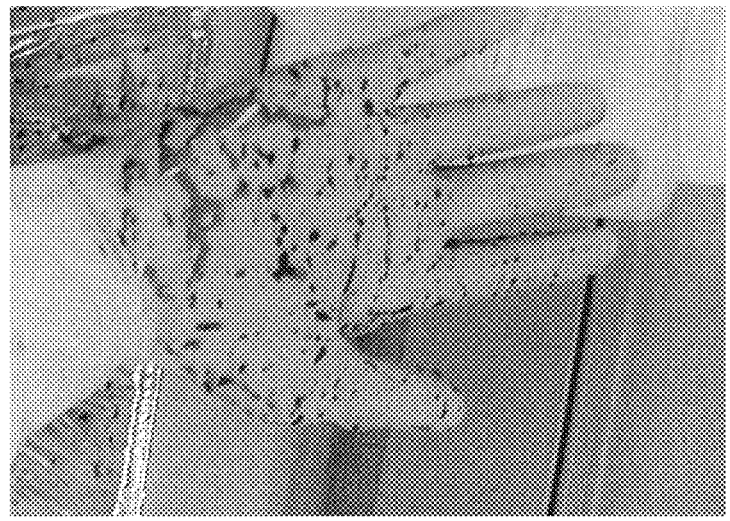
FIG. 11 is two photographs showing a sterile Protegrity® SMT natural rubber surgical glove treated according to one embodiment of the invention and a non-sterile Esteem® SMT polyisoprene surgical glove treated according to one embodiment of the invention, both samples having been subjected to accelerated age followed by the synthetic blood repellency test. See Example 52.
Figure 11:

Example 24 (Protegrity® SMT glove) and Example 27 (Esteem® SMT glove) as prepared in accordance with the invention and subjected to the accelerated age above were further subjected to the synthetic blood repellency test as shown in FIG. 11. As can be seen from the photographs, both the Protegrity® SMT and Esteem® SMT gloves exhibited desirable repellency characteristics.

Example 53

Figure 13:
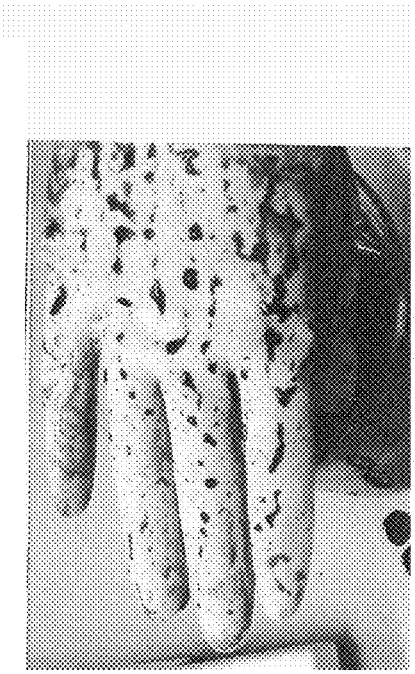
FIG. 13 is two photographs showing a Protegrity® SMT natural rubber surgical glove treated according to one embodiment of the invention and an Esteem® SMT polyisoprene surgical glove treated according to one embodiment of the invention, both samples having been subjected to further sterilization followed by the synthetic blood repellency test. See Example 53.
Figure 13:

Example 30 (Protegrity® SMT glove) and Example 33 (Esteem® SMT glove) as prepared in accordance with the invention and subjected to sterilization were further subjected to the synthetic blood repellency test as shown in FIG. 13. As can be seen from the photographs, both the Protegrity® SMT and Esteem® SMT gloves exhibited significant and substantial synthetic blood repellency characteristics.

Example 54

Example 20 (Protegrity®) and untreated control and Example 21 (Esteem®) and untreated control were subjected to the synthetic blood repellency test using a procedure similar to that described in Example 51 above. The gloves were immersed in the synthetic blood to coat their entire surfaces, and removed. Upon removal, the gloves were observed and photographed.

Figure 18:
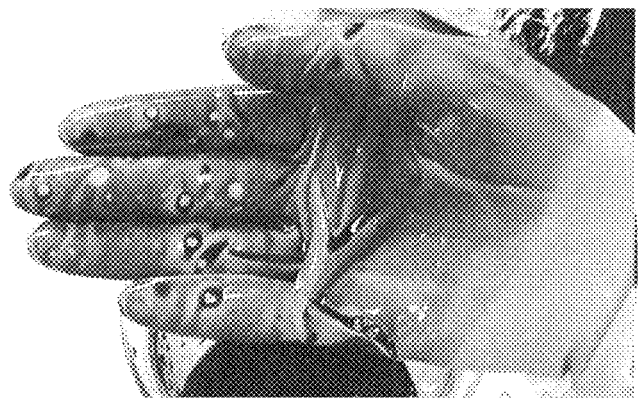
FIG. 18 is two photographs showing a sterile Protegrity® natural rubber surgical glove untreated and another sterile Protegrity® natural rubber surgical glove treated according to the invention, both gloves having been subjected to the synthetic blood repellency test. See Example 54.
Figure 18:
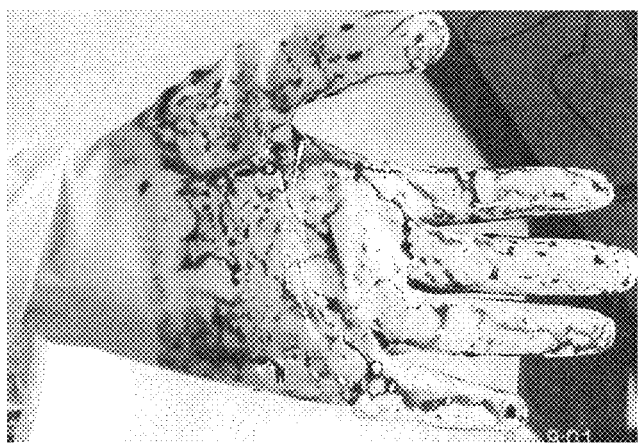
Figure 19:
FIG. 19 is two photographs showing a sterile Esteem® polyisoprene surgical glove untreated and another sterile Esteem® polyisoprene surgical glove treated according to the invention, both gloves having been subjected to the synthetic blood repellency test. See Example 54.
Figure 19:
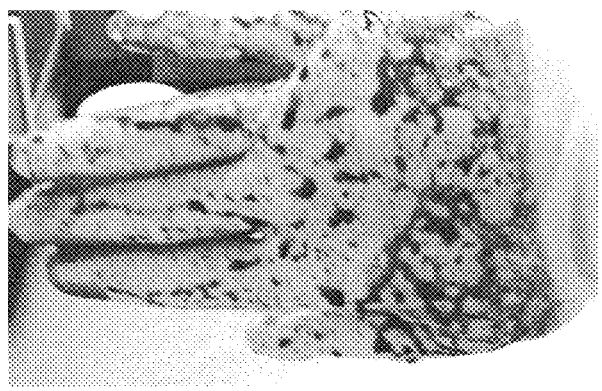

FIG. 18 shows the appearance of both Example 20 (Protegrity®) and an untreated control samples after the synthetic blood repellency test. Likewise, FIG. 19 shows the appearance of Example 21 (Esteem®) and an untreated control. Clearly, the presence of synthetic blood is significantly higher on the untreated gloves, and is in the form of a continuous coating over the glove surfaces. In contrast, the gloves prepared in accordance with the invention exhibit significantly less surface presence of synthetic blood on their surfaces, and the synthetic blood remaining is in the form of comparatively reduced size beads.

Example 55

In the previous examples, application of the repellent formulation to the glove in the laboratory provides excellent repellent performance. The industrial application of this process to a surgical glove requires certain factors to be taken into consideration, such as the effect of lubricant application on repellent performance and the ability to provide generally good glove performance such as donning ability. The following example will demonstrate the process feasibility by examining the application of lubricant prior to repellent treatment on the patient side of the surgical glove and the migration of trace amounts of repellent formulation (Example 8) to the donning side of the surgical glove. The process that will be described in this example is a laboratory-simulation of the production process.

For surgical glove applications, the gloves are preferably lubricated after chlorination with a lubricant formulation that provides good donning characteristics with respect to damp and wet skin. Those skilled in the in the art would apply the lubricant solution to the glove surface using such techniques as spraying or tumbling. The lubrication solution consists of about 0.1% wt. % to about 2 wt. % cetylpyridinium chloride (Zeeland Chemical, Zeeland, Mich.), about 0.01% to about 2 wt. % polydimethylsiloxane dispersion, such as GE SM2140™ (GE Silicones, Waterford, N.Y.) and about 0.1% wt. % to about 2 wt. % phosphate salts such as ammonium alkyl phosphate such as Darvan L™ (R.T. Vanderbilt, Norwalk, Conn.). Typically, after the lubricant application, the gloves are dried at about 55° C. for about 20 min. After the first dry, the gloves are turned inside out so that the coated surfaces are on the inside of the glove. The gloves are then further dried at about 50° C. for about 5 min. (The process for repellent application can be found in Example 8).

The purpose of this section is to demonstrate that application of lubricant prior to repellent treatment on the glove does not significantly impact the repellent glove performance and donning performance. Polyisoprene gloves pre-treated with lubricant solution described in the manner above were sprayed on the patient side with the repellent solution (Example 8) and placed in an oven to dry for 10 min at 90° C.

Figure 23:
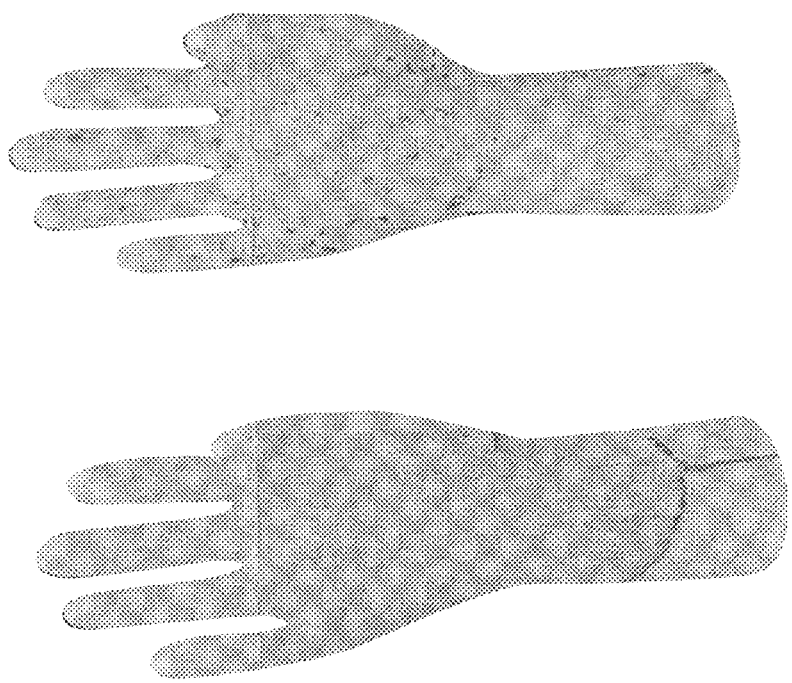
FIG. 23 is a photograph showing lubricant-and-repellent treated versus lubricant-treated gloves. See Example 55.
Figure 22:
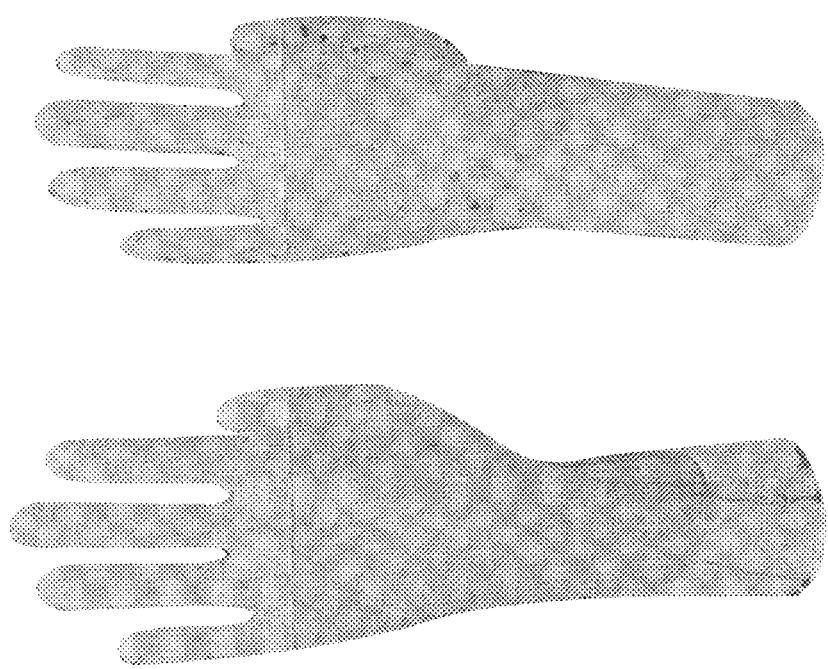
FIG. 22 is a photograph showing repellent-treated versus non-repellent treated gloves. See Example 55.

Then, the treated gloves' water repellency was evaluated using both a contact angle evaluation (described in Example 39) and a water repellency test (described in Example 44). The results were compared with polyisoprene gloves without lubricant and with/without repellent treatment. The results are set forth in the Table 55-1 and FIGS. 22-23 below:

| Table for Example 55-1 | | | | | |
|---|---|---|---|---|---|
| | | Qualitative Figure | Contact Angle | | |
| Sample | Description | Reference | 0 min | 5 min | 15 min |
| Sample 34 | Non-Treated glove | 22 (left) | 68° | 67° | 33° |
| Sample 35 | Repellent-treated glove | 22 (right) | 105° | 100° | 94° |
| Sample 36 | Lubricant-Treated glove | 23 (left) | 78° | 29° | 16° |
| Sample 37 | Repellent and lubricant-treated glove | 23 (right) | 93° | 91° | 88° |

The contact angle of Sample 37 is sustained for at least 15 min and is significantly better than the lubricated glove without repellent treatment, Sample 36. Thus, the lubricated glove treated with the repellent formulation of this invention, Sample 37, provides good water repellency (as described in the detailed description of this invention). The repellency performance and contact angle are sustained when lubricant is applied prior to the spraying of the glove with repellent formulation. See FIGS. 22 and 23.

The application (tumbling/spraying) of the repellent formulation (Example 8) to the glove in the manufacturing process, may allow trace amounts of repellent solution to migrate to the donning side of the glove. The purpose of this test is to demonstrate that these trace amounts of repellent formulation on to the donning side of the glove do not adversely affect the donning performance of the glove. The simulation of this process involved spraying the donning side of the glove with repellent formulation (Example 8) and drying it at 90° C. for 10 min. In a blind evaluation study, three individuals were instructed to dampen their hands and wrists thoroughly with water, don three pairs of gloves, and evaluate their donningability. Each pair consisted of a lubricated glove with repellent on the donning side (Sample 38) and a lubricated glove without repellent on the donning side (Sample 39). The results of this study are set forth in Table 55-2.

| Table of Example 55-2 | | | |
|---|---|---|---|
| Sample | Description | Acceptable Donning | Unacceptable Donning |
| Sample 38 | Lubricated glove with repellent on donning side | 5 | 1 |
| Sample 39 | Lubricated glove without repellent on donning side | 5 | 1 |

This simulation of the repellent formulation (Example 8) being applied to the donning side of the glove, Example 38, demonstrates an acceptable donning performance. Thus, the repellent formulation does not adversely affect the donning ability of the glove. Hence, both the repellent and donning performance of an industrially produced glove (where the lubricant is applied prior to repellent treatment) is maintained.

Example 56

The method within this example addresses the lack of adherence of microorganisms to the surface of a glove as a result of being treated with the repellent formulation of this invention (Example 8). The reduction in the microbial titer is a result of repelling contaminated fluids from the surface of the repellent-treated glove. This is explained as a lack of adhesion of microbes to the surface of the glove and hence, a lower microbial titer and a reduced fluid-based risk of contamination. In this example, a bacterial spore suspension of $B.$ $subtitles$ var. $niger$ was diluted to final inoculum level of $1.00 \times 10^7$ CFU/ml. One milliliter of this dilution was aseptically spread on a sterile glass surface. Three pieces (4×4 cm) from three sterilized treated gloves and three (3) control pieces from three (3) non-coated gloves were applied on the contaminated surface, facing it with the coated side for 30 sec. The transmitted spores were extracted then in 10 ml sterile phosphate buffer solution and employed by the Standard Plate Count Method. The percent recovery of the transmitted CFU/ml per each testing sample was calculated. Natural rubber latex surgical gloves accelerated for 7 days at 70° C. were used for testing purpose. The following non-limiting examples further illustrate the invention.

The results are summarized in the following tables:

| Table 1 for Example 56 | | | | |
|---|---|---|---|---|
| Sample | Glove Description | Titer of Potential Present Spores/CFU/ml | Titer of Transmitted Spores/CFU/ml | % Recovery |
| Example 40 | Treated | $1.54 \times 10^6$ | $2.36 \times 10^4$ | 1.53 |
| Example 41 | Control/Untreated | $1.54 \times 10^6$ | $4.25 \times 10^4$ | 2.76 |

There was a significant reduction of 44.57% in the microbial affinity of the treated gloves vs. non-treated ones when a glass substrate was used for testing purpose.

| Table 2 for Example 56 | | | | |
|---|---|---|---|---|
| Sample | Glove Description | Titer of Potential Present Spores/CFU/ml | Titer of Transmitted Spores/CFU/ml | % Recovery |
| Example 42 | Treated | $3.50 \times 10^6$ | $5.50 \times 10^4$ | 1.57 |
| Example 43 | Control/Untreated | $3.50 \times 10^6$ | $1.27 \times 10^5$ | 3.62 |

The treated articles had 56.63% higher reduction in the microbial transmission level compared to non-treated articles when the test was repeated.

INDUSTRIAL APPLICABILITY

The above figures demonstrate one of the major advantages of the invention of repelling liquids such as blood from an article surface. In biologically and chemically hazardous contexts of usage, articles such as gloves when made according to the invention reduce the likelihood of unintentional contact with such fluids. Therefore, the risk of injury or contamination to the user wearing such articles is also significantly reduced.

The invention is useful in a variety of applications where elastomeric articles are to be worn and a mixture of hydrophilic and lipophilic liquids are likely to be encountered. Thus, the invention can be used in conjunction with articles such as industrial gloves and medical gloves. The invention is particularly useful with medical gloves, such examination and surgical gloves, where reducing the visual and physical interference of fluids and eliminating the need to replace gloves during a procedure, are practical and/or aesthetic advantages.

The invention has been described herein above with reference to various and specific embodiments and techniques. It will be understood, however, that reasonable modifications of such embodiments and techniques can be made without substantially departing from either the spirit or scope of the invention defined by the following claims.

What is claimed is:
1. A method of reducing microbial adherence to the surface of an elastomeric article formed from an elastomer selected from the group consisting of natural rubber, synthetic polyisoprene, nitrile, polyvinyl chloride, acrylic copolymers, butyl rubbers, styrene block co-polymers, polyurethane, and combinations thereof, comprising:
   chlorinating the elastomeric article; and applying a fluid repellent coating composition to the surface of the elastomeric article, wherein said coating composition comprises a low surface energy ingredient and a wax;

wherein the elastomeric article exhibits reduced adherence of microbes to the surface of the elastomeric article compared to an identical elastomeric article without the coating composition.

2. The method according to claim 1, wherein the reduction in microbial adherence is greater than about 40% as measured by microbial titer of the surface of the elastomeric article.

3. The method according to claim 1, wherein the reduction in microbial adherence is greater than about 50% as measured by microbial titer of the surface of the elastomeric article.

4. The method according to claim 1, wherein the microbial adherence of Gram positive bacteria is reduced.

5. The method according to claim 1, wherein the microbial adherence of Gram negative bacteria is reduced.

6. The method according to claim 1, wherein the microbial adherence of *B. subtiles* var. *niger* is reduced.

7. The method according to claim 1, wherein said elastomeric article is a medical glove.

8. The method according to claim 7, wherein said medical glove is an examination glove.

9. The method according to claim 7, wherein said medical glove is a surgical glove.

10. The method according to claim 1, wherein said elastomeric article comprises natural rubber.

11. The method according to claim 1, wherein said elastomeric article comprises synthetic rubber.

12. The method according to claim 11, wherein said synthetic rubber is nitrile rubber.

13. The method according to claim 11, wherein said synthetic rubber is synthetic polyisoprene.

14. The method according to claim 1, wherein said fluid repellent coating composition applied to the surface of an elastomeric article repels liquid contaminated with bacteria from the surface of the elastomeric article.

15. The method according to claim 1, wherein said fluid repellent coating composition applied to the surface of an elastomeric article repels blood, synthetic blood, and/or a bodily fluid from the surface of the elastomeric article.

16. An elastomeric article comprising a chlorinated elastomeric base formed from an elastomer selected from the group consisting of natural rubber, synthetic polyisoprene, nitrile, polyvinyl chloride, acrylic copolymers, butyl rubbers, styrene block co-polymers, polyurethane, and combinations thereof and a fluid repellent surface coating composition provided thereon, said coating composition comprising:

a) a low surface energy ingredient, and b) a wax;

wherein the elastomeric article exhibits reduced adherence of microbes to the surface of the elastomeric article compared to an identical elastomeric article without the coating composition.

17. The elastomeric article according to claim 16, wherein the reduction in adherence of microbes to the surface of the elastomeric article is greater than about 40% as measured by microbial titer of the surface of the elastomeric article.

18. The elastomeric article according to claim 16, wherein the reduction in adherence of microbes to the surface of the elastomeric article is greater than about 50% as measured by microbial titer of the surface of the elastomeric article.

19. The elastomeric article according to claim 16, wherein the microbial adherence of Gram positive bacteria is reduced.

20. The elastomeric article according to claim 16, wherein the microbial adherence of Gram negative bacteria is reduced.

21. The elastomeric article according to claim 16, wherein the microbial adherence of *B. subtiles* var. *niger* is reduced.

22. The elastomeric article according to claim 16, wherein said article is a medical glove.

23. The elastomeric article according to claim 22, wherein said medical glove is an examination glove.

24. The elastomeric article according to claim 22, wherein said medical glove is a surgical glove.

25. The elastomeric article according to claim 16, wherein the coating composition is present on at least the exterior surface of the elastomeric article.

26. The elastomeric article according to claim 25, wherein the exterior surface of the elastomeric article exhibits grip properties that are not compromised as compared to an untreated elastomeric article.

* * * * *